(12) United States Patent
North

(10) Patent No.: US 8,311,643 B2
(45) Date of Patent: Nov. 13, 2012

(54) SPINAL CORD STIMULATION LEAD ANCHOR

(76) Inventor: Richard B. North, Baltimore, MD (US)

( * ) Notice: Subject to any disclaimer, the term of this patent is extended or adjusted under 35 U.S.C. 154(b) by 23 days.

(21) Appl. No.: 12/804,403

(22) Filed: Jul. 21, 2010

(65) Prior Publication Data

US 2011/0022143 A1 Jan. 27, 2011

Related U.S. Application Data

(60) Provisional application No. 61/227,136, filed on Jul. 21, 2009.

(51) Int. Cl.
*A61N 1/00* (2006.01)
(52) U.S. Cl. ............ 607/117; 607/37; 607/126
(58) Field of Classification Search ............ 607/37, 607/117, 126
See application file for complete search history.

(56) References Cited

U.S. PATENT DOCUMENTS

| | | | |
|---|---|---|---|
| 4,590,949 A | 5/1986 | Pohndorf | |
| 5,376,108 A | 12/1994 | Collins et al. | |
| 5,484,445 A | 1/1996 | Knuth | |
| 5,733,322 A | 3/1998 | Starkebaum | |
| 6,308,103 B1 | 10/2001 | Gielen | |
| 6,554,802 B1 | 4/2003 | Pearson et al. | |
| 6,879,854 B2 | 4/2005 | Windheuser et al. | |
| 6,978,180 B2 | 12/2005 | Tadlock | |
| 6,999,819 B2 | 2/2006 | Swoyer et al. | |
| 7,099,718 B1 | 8/2006 | Thacker et al. | |
| 7,270,650 B2 | 9/2007 | Morris et al. | |
| 7,330,764 B2 | 2/2008 | Swoyer et al. | |
| 7,610,102 B2 | 10/2009 | Kowalczyk | |
| 7,831,313 B2 | 11/2010 | Lauro | |
| 2005/0065570 A1* | 3/2005 | Stein et al. | 607/37 |
| 2005/0096718 A1 | 5/2005 | Gerber et al. | |
| 2006/0127158 A1 | 6/2006 | Olson et al. | |
| 2006/0173520 A1 | 8/2006 | Olson | |
| 2006/0253088 A1 | 11/2006 | Chow et al. | |
| 2008/0243220 A1 | 10/2008 | Barker | |
| 2009/0088725 A1* | 4/2009 | Bataille et al. | 604/509 |

OTHER PUBLICATIONS

Violette M. Renard, M.D. and Richard B. North, M.D., "Prevention of percutaneous electrode migration in spinal cord stimulation by a modification of the standard implantation technique," J. Neurosurg: Spine, vol. 4:300-303 (Apr. 2006).

* cited by examiner

*Primary Examiner* — Nicole F Lavert
(74) *Attorney, Agent, or Firm* — Whiteford, Taylor & Preston LLP

(57) ABSTRACT

Disclosed is an implantable anchor for anchoring a catheter, including (by way of non-limiting example) an implantable lead, such as may be used for spinal cord stimulation, to the body of a patient, along with a method for its use. The anchor comprises an elongate body have a central lumen extending through the body from its proximal end to its distal end, which central lumen is configured to snugly receive the catheter body. In addition to the central lumen, a second lumen is provided in the proximal end of the anchor and is configured to receive an injector so that adhesive may be injected into the anchor surrounding at least a portion of the catheter body. In doing so, the anchor may be fixed to the catheter body, such that when the anchor is sutured in place within the patient's body, migration of the catheter may be avoided.

19 Claims, 2 Drawing Sheets

SPINAL CORD STIMULATION LEAD ANCHOR

CROSS REFERENCE TO RELATED APPLICATION

This application is based upon and claims benefit of copending U.S. Provisional Patent Application Ser. No. 61/227,136 entitled "Spinal Cord Stimulation Lead Anchor", filed with the U.S. Patent and Trademark Office on Jul. 21, 2009 by the inventor herein, the specification of which is incorporated herein by reference.

FIELD OF THE INVENTION

The present invention relates generally to the field of implantable medical electronic devices, such as electrical stimulators, epidural electrodes, defibrillators and pacemakers, and more particularly to a method and tool for anchoring a catheter, such as a percutaneous spinal cord electrode, so as to prevent longitudinal migration after implantation.

BACKGROUND OF THE INVENTION

Percutaneous spinal cord stimulation ("SCS") electrodes are catheters having electrical contacts at their ends and wires running through them to transmit an electrical signal to those contacts from a power source. They are inserted into the spinal canal through needles and precisely positioned using fluoroscopic guidance and careful testing in an awake patient. Once a final position is verified, they are secured in position using an anchoring sleeve through which the electrode passes, and suturing the anchoring sleeve in place. Unfortunately, after several months in situ, such percutaneous electrodes are prone to migration, even after scar tissue encapsulates the electrode.

Previous attempts have been made to mitigate the tendency of electrodes to migrate after implantation. For instance, efforts have been made to introduce adhesive (e.g., biocompatible glue or caulk) to fill the dead space between the inside of the anchor and the outside of the lead or catheter. Unfortunately, however, injecting such adhesive into the miniscule dead space between the inside of the anchor and the outside of the lead or catheter is a very difficult task, as it is quite difficult to insert the tip of an injector between the outside of the lead or catheter and the inside of the silicone elastomer anchor. Moreover, such delicate maneuvers must be carried out at the bottom of a surgical wound, further complicating the effort.

It would therefore be advantageous to provide an improved device capable of anchoring a percutaneous SCS electrode or other catheter-type instrument without requiring such a difficult placement of an injector tip between the electrode or catheter and the interior of the anchor for introducing adhesive between the anchor and the electrode or catheter.

SUMMARY OF THE INVENTION

Disclosed is an implantable anchor for anchoring a catheter, including (by way of non-limiting example) an implantable lead, such as may be used for spinal cord stimulation, to the body of a patient, along with a method for its use. The anchor comprises an elongate body having a central lumen extending through the elongate body from its proximal end to its distal end, which central lumen is configured to snugly receive the catheter body. In addition to the central lumen, a second lumen is provided in the proximal end of the anchor and is configured to receive an injector so that adhesive may be injected into the anchor surrounding at least a portion of the catheter body. In doing so, the anchor may be fixed to the catheter body, such that when the anchor is sutured in place within the patient's body, migration of the catheter may be prevented.

With regard to a first aspect of the invention, an implantable anchor is provided comprising an anchoring sleeve body having a proximal end and a distal end, a central lumen extending through the body from the proximal end to the distal end and configured to receive a catheter therein, and a second lumen having a first end opening to the exterior of the body and a second end opposite the first end opening to the interior of the body and intersecting the central lumen.

With regard to another aspect of the invention, a lead assembly adapted to be implanted in and anchored to the body of a patient is provided, which assembly comprises a lead having a distal end comprising one or more electrodes and a proximal end configured for attachment to an implantable medical device and a generally cylindrical lead body extending between the distal end and the proximal end of the lead, and a lead anchor configured for anchoring the lead to a patient's body, the lead anchor comprising an anchoring sleeve body having a proximal end and a distal end opposite the proximal end and a central lumen extending through the anchoring sleeve body from the proximal end to the distal end, the central lumen having an internal diameter at least as large as an external diameter of the lead body and configured to receive the lead body therein, and a second lumen having a first end opening to the exterior of the anchoring sleeve body and a second end opposite the first end opening to the interior of the anchoring sleeve body and intersecting the central lumen, the second lumen having an internal diameter smaller than the external diameter of the lead body and configured to receive the tip of an adhesive injector.

With regard to a further aspect of the invention, a method for anchoring a catheter to a patient's body is provided, comprising the steps of: (i) providing a catheter having a distal free end configured for placement within a patient's body at a location requiring treatment and a proximal end configured for attachment to an implantable medical device, and a generally cylindrical catheter body extending between the distal end and the proximal end; (ii) providing an implantable anchor configured for anchoring the catheter to a patient's body, the anchor further comprising an anchoring sleeve body having a proximal end and a distal end opposite the proximal end and a central lumen extending through the anchoring sleeve body from the proximal end to the distal end, the central lumen having an internal diameter at least as large as an external diameter of the catheter body and configured to receive the catheter body therein, and a second lumen having a first end opening to the exterior of the anchoring sleeve body and a second end opposite the first end opening to the interior of the anchoring sleeve body and intersecting the central lumen, the second lumen having an internal diameter smaller than the external diameter of the catheter body and configured to receive the tip of an adhesive injector therein; (iii) inserting the distal free end of the catheter through the anchoring sleeve body from the proximal end to the distal end; and (iv) injecting an adhesive into the second lumen so as to affix the anchoring sleeve to the catheter body.

BRIEF DESCRIPTION OF THE DRAWINGS

The numerous advantages of the present invention may be better understood by those skilled in the art by reference to the accompanying drawings in which.

DETAILED DESCRIPTION OF THE INVENTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
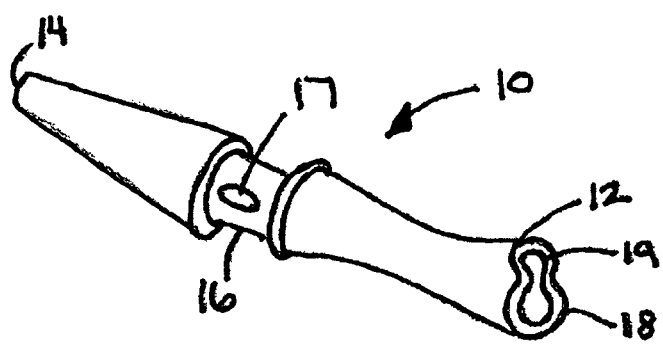
FIG. 1 is a perspective view of an implantable anchor according to certain aspects of a particularly preferred embodiment of the invention.
Figure 2:
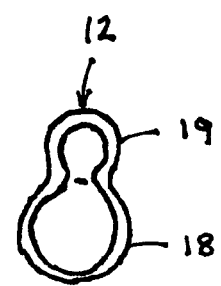
FIG. 2 is an end view of the implantable anchor of FIG. 1.
Figure 3:
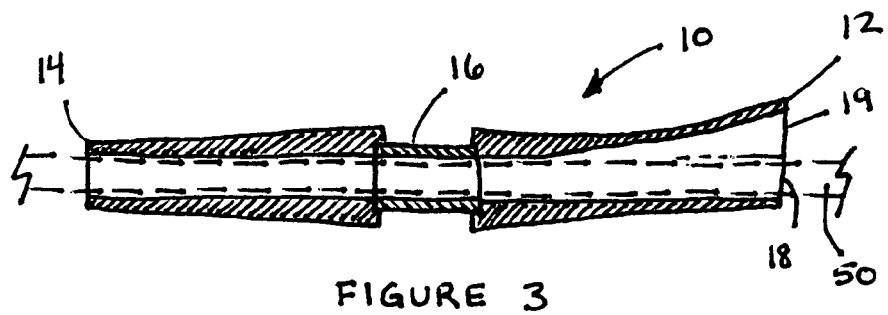
FIG. 3 is a side, sectional view of the anchor of FIG. 1.

With regard to a particularly preferred embodiment of the invention, an improved anchor is provided that is particularly configured to aid in the introduction of adhesive between the interior of the anchor and the exterior of a catheter, such as a lead configured for use as an SCS electrode, so as to improve the adhesion of the lead to the anchor, thereby limiting if not altogether preventing migration. As shown in FIGS. 1-3, a lead anchor (shown generally at 10) is provided having a proximal end 12 and a distal end 14, joined to one another by a generally cylindrical central portion 16. While distal end 14 may be provided a traditional, generally circular opening through which the lead 50 passes, proximal end 12 is provided a flared configuration having a lower, generally circular portion 18 and a smaller upper, generally circular portion 19. As shown in FIGS. 1-3, the top of lower circular portion 18 and the bottom of upper circular portion 19 may open into one another, thus forming a continuous opening. Lower circular portion 18 is preferably configured to closely approximate the outer diameter of the lead 50, and when in use, the lead 50 may be positioned in anchor 10 extending through lower circular portion 18, cylindrical central portion 16, and distal end 14 from which it exits anchor 10. Even with the lead 50 so positioned within anchor 10, upper circular portion 19 of proximal end 12 remains open, thus forming a receiving channel configured to receive the tip of an injector, such as a small syringe. As adhesive is injected into upper circular portion 19 of proximal end 12, it will progress forward through anchor 10 around at least a portion of lead 50 and towards the distal end 14. Central cylindrical portion 16 is preferably provided a vent 17 opening to the interior of anchor 10, which vent 17 may allow egress of excess adhesive from the interior of anchor 10, in turn serving as a visual indicator that the adhesive injection has been successful.

Figure 4:
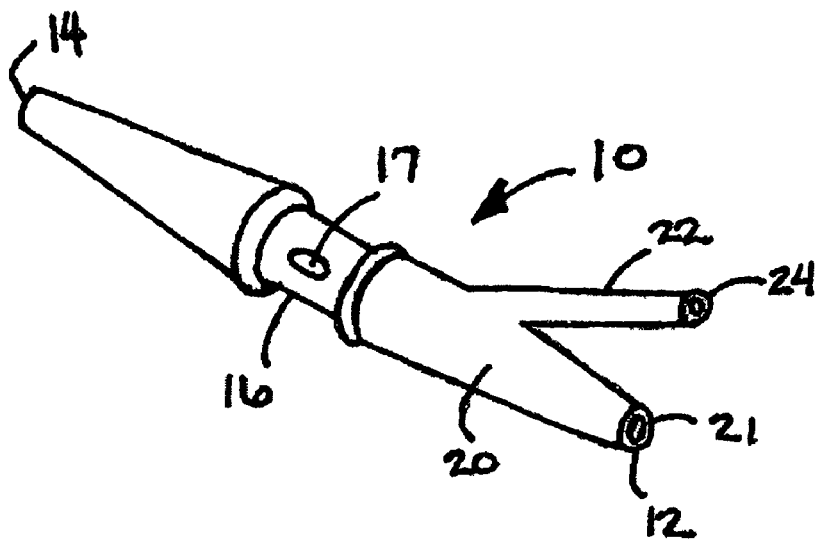
FIG. 4 is a perspective view of an implantable anchor according to further aspects of a particularly preferred embodiment of the invention.
Figure 5:
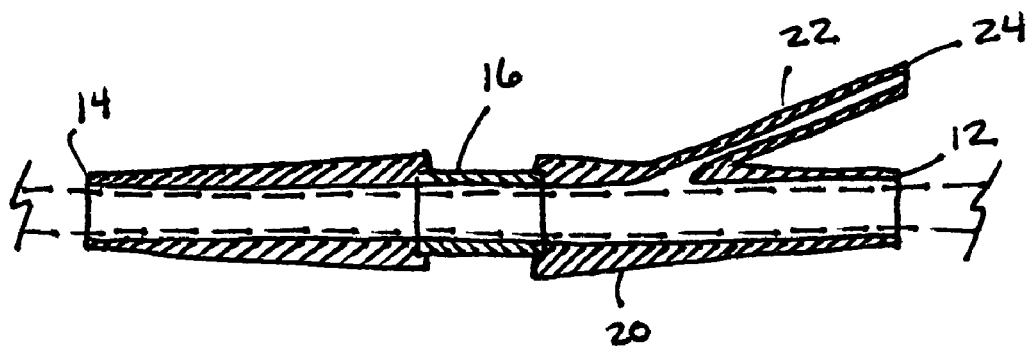
FIG. 5 is a side, sectional view of the anchor of FIG. 4.

With respect to a first alternative embodiment and as shown in FIGS. 4-5, anchor 10 may be provided an independent bore 22, which bore 22 diverges from a main body portion 20. Main body portion 20 terminates at proximal end 12 of anchor 10 in an opening 21 configured to closely approximate the outer diameter of the lead 50. Bore 22, in turn, extends away from main body portion 20 but in a direction generally towards proximal end 12 of anchor 10, and terminates in an opening 24 configured to receive the tip of an injector, such as a small syringe. As with the embodiment depicted in FIG. 1, as adhesive is injected into bore 22 through opening 24, it will progress downward through bore 22 and into main body portion 20 of anchor 10, at which point it will flow around at least a portion of lead 50 and towards both proximal end 12 and distal end 14 of anchor 10. Central cylindrical portion 16 of anchor 10 is once again provided a vent 17 opening to the interior of anchor 10, which vent 17 may allow egress of excess adhesive from the interior of anchor 10, in turn serving as a visual indicator that the adhesive injection has been successful.

As those of ordinary skill in the art will recognize, bore 22 need not terminate immediately adjacent opening 21, and in fact may extend significantly further away from main body portion 20 than what is depicted in FIG. 2, thus easing the introduction of adhesive into anchor 10 by allowing its introduction at a location that is distant from the operative site at which the anchor is implanted.

With regard to another aspect of a particularly preferred embodiment of the invention, bore 22 may be provided tubing or plumbing connections at its terminal end (i.e., at opening 24), such as a fitting to facilitate the connection to a syringe or to receive the tip of a tube of adhesive. For instance, a Luer lock of traditional configuration may be provided at the terminal end of bore 22 to directly receive a syringe containing adhesive that is to be injected into anchor 10. Alternatively, a threaded connector may be provided at the terminal end of bore 22 to directly receive a threaded tip of a tube of adhesive. Other such connections could likewise be used as will be apparent to those of ordinary skill in the art. When using such a connector, after the adhesive has been injected into anchor 10 (as confirmed by the egress of adhesive from vent 17 in central cylindrical portion 16 of anchor 10), the extended portion of bore 22 (including any such fittings configured to receive a syringe or tube of adhesive) may be cut away from the remainder of anchor 10 and discarded.

Those of ordinary skill in the art will recognize that while the configurations depicted in the foregoing Figures show an anchor configured with openings to receive a single lead 50, provision could be made, and anchor 10 could be so modified, so as to allow for the introduction of multiple leads in a single anchor, such as by widening the openings at each of proximal end 12 and distal end 14 of anchor 10, with the particular port for receiving an adhesive injector being in fluid communication with the channel through anchor 10 through which such multiple leads pass.

Moreover, those of ordinary skill in the art will also recognize that devices other than lead 50 may be similarly anchored using the anchor of the instant invention, such as catheters of all types.

It shall be understood that various other characteristics of the novel anchor of the current invention and its method of use may be changed without departing from the scope and spirit of the present invention. For instance, the material composition of the anchor may comprise a silicone elastomer, or alternatively other plastic, metal, or other materials, so long as such material is biologically inert. Moreover, different sections or pieces of the anchor may be similar or of different material composition from one another. In addition, while the exemplary embodiments show an anchor having particular proportions, it is contemplated that the anchor may include varying proportions or configurations.

It is believed that the present invention and many of its attendant advantages will be understood by the forgoing description. It is also believed that it will be apparent that various changes may be made in the form, construction and arrangement of the components thereof without departing from the spirit and scope of the invention or without sacrificing all of its material advantages. The form herein before described is merely an explanatory embodiment thereof.

I claim:

1. An implantable anchor for anchoring a catheter to a patient's body, comprising:

an implantable anchoring sleeve body having a proximal end, a distal end opposite said proximal end, a proximal body portion adjacent said proximal end, a distal body portion adjacent said distal end, a central body portion between said proximal body portion and said distal body portion, and a central lumen extending through said proximal body portion, said central body portion, and said distal body portion from said proximal end to said distal end and configured to receive a catheter therein;

a second lumen having a first end opening to the exterior of said anchoring sleeve body, and a second end opposite said first end opening to the interior of said anchoring sleeve body and intersecting said central lumen, wherein said second lumen is configured to deliver an adhesive to at least a portion of a catheter placed within said central lumen, and a vent centrally located between said distal end and said proximal end;

wherein said second lumen is configured to receive an adhesive injector and to direct adhesive injected therefrom around at least a portion of a catheter positioned within said central lumen, and wherein said vent extends from the exterior of said central lumen to the interior of said central lumen and is located in said central body portion.

2. The implantable anchor of claim 1, wherein said first end of said second lumen extends away from said anchoring sleeve body in a direction generally toward said proximal end of said body.

3. The implantable anchor of claim 2, wherein a top portion of said central lumen adjacent said proximal end of said central lumen opens into a bottom portion of said second lumen at said first end of said second lumen.

4. The implantable anchor of claim 2, wherein said second lumen further comprises an independent bore from said central lumen extending upward and away from said central lumen.

5. The implantable anchor of claim 1, wherein said anchor is configured to allow adhesive injected from an adhesive injector to flow around said catheter and to said vent to provide a visual indication of the presence of adhesive within said central body portion.

6. A lead assembly adapted to be implanted in and anchored to a body of a patient, comprising:

a lead having a distal end comprising one or more electrodes and a proximal end configured for attachment to an implantable medical device, and a cylindrical lead body extending between said distal end and said proximal end; and a lead anchor configured for anchoring said lead to a patient's body, said lead anchor further comprising an implantable anchoring sleeve body having a proximal end, a distal end opposite said proximal end, a proximal body portion adjacent said proximal end, a distal body portion adjacent said distal end, a central body portion between said proximal body portion and said distal body portion, and a central lumen extending through said proximal body portion, said central body portion, and said distal body portion from said proximal end to said distal end, said central lumen having an internal diameter at least as large as an external diameter of said lead body and configured to receive said lead body therein;

a second lumen having a first end opening to the exterior of said anchoring sleeve body, and a second end opposite said first end opening to the interior of said anchoring sleeve body and intersecting said central lumen, said second lumen having an internal diameter smaller than said external diameter of said lead body and configured to receive the tip of an adhesive injector therein; and a vent centrally located between said distal end and said proximal end;

wherein said second lumen is configured to receive an adhesive injector and to direct adhesive injected therefrom around at least a portion of said lead, and wherein said vent extends from the exterior of said central lumen to the interior of said central lumen and is located in said central body portion.

7. The lead assembly of claim 6, wherein said first end of said second lumen extends away from said anchoring sleeve body in a direction generally toward said proximal end of said anchoring sleeve body.

8. The lead assembly of claim 7, wherein a top portion of said central lumen adjacent said proximal end of said central lumen opens into a bottom portion of said second lumen at said first end of said second lumen.

9. The lead assembly of claim 7, wherein said second lumen further comprises an independent bore from said central lumen extending upward and away from said central lumen.

10. The lead assembly of claim 6, wherein said lead anchor is configured to allow adhesive injected from an adhesive injector to flow around said cylindrical lead body and to said vent to provide a visual indication of the presence of adhesive within said central body portion of said anchoring sleeve body.

11. A method for anchoring a catheter to a patient's body, comprising:

providing a catheter having a distal free end configured for placement within a patient's body at a location requiring treatment, and a catheter proximal end configured for attachment to an implantable medical device, and a cylindrical catheter body extending between said distal free end and said catheter proximal end;

providing an implantable anchor configured for anchoring the catheter to a patient's body, said anchor further comprising;

an implantable anchoring sleeve body having a proximal end, a distal end opposite said proximal end, a proximal body portion adjacent said proximal end, a distal body portion adjacent said distal end, a central body portion between said proximal body portion and said distal body portion, and a central lumen extending through said proximal body portion, said central body portion, and said distal body portion from said proximal end to said distal end, said central lumen having an internal diameter at least as large as an external diameter of said catheter body and configured to receive said catheter body therein;

a second lumen having a first end opening to the exterior of said anchoring sleeve body, and a second end opposite said first end opening to the interior of said anchoring sleeve body and intersecting said central lumen, said second lumen having an internal diameter smaller than said external diameter of said catheter body and configured to receive the tip of an adhesive injector therein; and a vent centrally located between said distal end and said proximal wherein said second lumen is configured to receive an adhesive injector and to direct adhesive injected therefrom around at least a portion of a catheter positioned within said central lumen, and wherein said vent extends from the exterior of said central lumen to the interior of said central lumen and is located in said central body portion;

inserting said distal free end of said catheter through said anchoring sleeve body from said proximal end to said distal end; and injecting an adhesive into said second lumen so as to affix said implantable anchoring sleeve to said catheter body.

12. The method of claim 11, wherein said injecting step directs said adhesive around at least a portion of said catheter body positioned within said central lumen.

13. The method of claim 12, further comprising the step of continuing said injection of adhesive until said adhesive is visible in said vent.

14. The method of claim 13, further comprising the step of cutting off a portion of said second lumen after said injection step is completed.

15. The method of claim 11, further comprising implanting said implantable anchor at a location in a patient's body.

16. An implantable anchor for anchoring a catheter to a patient's body, comprising:

an implantable anchoring sleeve body having a proximal end, a distal end opposite said proximal end, a proximal body portion adjacent said proximal end, a distal body portion adjacent said distal end, a central body portion between said proximal body portion and said distal body portion, and a central lumen extending through said proximal body portion, said central body portion, and said distal body portion; and a second lumen having a second lumen proximal end opening to the exterior of said anchoring sleeve body at said anchoring sleeve body proximal end, and a second lumen distal end opposite said second lumen proximal end opening to the interior of said anchoring sleeve body and intersecting said central lumen, wherein said second lumen is configured to receive an adhesive injector and to direct adhesive injected therefrom around at least a portion of a catheter positioned within said central lumen;

wherein at least a portion of an outer perimeter of said central lumen opens into an interior portion of said second lumen at said proximal ends of said central lumen and said second lumen.

17. The implantable anchor of claim 16, further comprising: a vent centrally located between said distal end and said proximal end of said anchoring sleeve body.

18. The implantable anchor of claim 17, wherein said vent extends from the exterior of said central lumen to the interior of said central lumen and is located in said central body portion.

19. The implantable anchor of claim 18, wherein said anchor is configured to allow adhesive injected from an adhesive injector to flow around said catheter and to said vent to provide a visual indication of the presence of adhesive within said central body portion.

* * * * *